US012629306B2

(12) United States Patent
Hofer et al.

(10) Patent No.: US 12,629,306 B2
(45) Date of Patent: May 19, 2026

(54) COMPOSITION FOR PRODUCTION OF A TEST SOIL FOR ASSESSMENT OF THE CLEANING ACTION OF CLEANING DEVICES AND USE THEREOF

(71) Applicant: MEIKO Maschinenbau GmbH & Co. KG, Offenburg (DE)

(72) Inventors: Martin Hofer, Durbach (DE); Marijan Simundic, Ohlsbach (DE)

(73) Assignee: MEIKO Maschinenbau GmbH & Co. KG, Offenburg (DE)

( * ) Notice: Subject to any disclaimer, the term of this patent is extended or adjusted under 35 U.S.C. 154(b) by 998 days.

(21) Appl. No.: 17/625,653

(22) PCT Filed: Jul. 8, 2020

(86) PCT No.: PCT/EP2020/069257
§ 371 (c)(1),
(2) Date: Jan. 7, 2022

(87) PCT Pub. No.: WO2021/005111
PCT Pub. Date: Jan. 14, 2021

(65) Prior Publication Data
US 2022/0362082 A1      Nov. 17, 2022

(30) Foreign Application Priority Data

Jul. 9, 2019    (DE) ..................... 10 2019 210 089.9

(51) Int. Cl.
*A61G 9/02*        (2006.01)
*A23L 15/00*       (2026.01)
(Continued)

(52) U.S. Cl.
CPC .................. *A61G 9/02* (2013.01); *B08B 9/46* (2013.01); *B08B 13/00* (2013.01); *A23L 15/35* (2016.08);
(Continued)

(58) Field of Classification Search
CPC .. A61G 9/02; B08B 9/46; B08B 13/00; B08B 2209/08; A23L 15/35; A61B 2090/702; A61B 90/96; A61B 90/98; G01N 31/22
See application file for complete search history.

(56) References Cited

U.S. PATENT DOCUMENTS 3,640,731 A * 2/1972 Kaplow .................. A23L 15/20
426/599
4,094,996 A * 6/1978 Sakakibara .......... B65D 85/816
426/115
(Continued)

FOREIGN PATENT DOCUMENTS

CN        106370222 A * 2/2017 ............. G01D 21/00
DE        196 02 673 A1    8/1997
(Continued)

OTHER PUBLICATIONS

OEGSV (Austrian Society for Sterile Supplies, "ANNEX 1 to Guidelines for Testing, Validation and Monitoring of Automated Cleaning and Disinfection Processes for Medical Devices", Apr. 2005). (Year: 2005).*
(Continued)

*Primary Examiner* — Binh X Tran
*Assistant Examiner* — Christopher Remavege
(74) *Attorney, Agent, or Firm* — Oblon, McClelland, Maier & Neustadt, L.L.P.

(57) ABSTRACT

A composition may include, in dry form: (a) nigrosin; (b) wheat flour; and (c) whole egg. Such compositions may be used for production of test soil for assessment of the cleaning action of cleaning devices. Methods of producing a test soil for assessment of the cleaning action of cleaning devices for cleaning of vessels for human egesta, e.g., of washer-disinfectors, including dissolving the composition in an aqueous medium. A test soil may include the constituents of the composition in an aqueous medium, and such soils (Continued)

(A)

(B)

may be used for assessment of the cleaning action of cleaning devices. A method may assess the cleaning action of cleaning devices for cleaning of vessels for human egesta.

20 Claims, 1 Drawing Sheet

(51) Int. Cl.
*A61B 90/70* (2016.01)
*B08B 9/46* (2006.01)
*B08B 13/00* (2006.01)

(52) U.S. Cl.
CPC ..... *A61B 2090/702* (2016.02); *B08B 2209/08* (2013.01)

(56) References Cited

U.S. PATENT DOCUMENTS

| | | | |
|---|---|---|---|
| 6,107,097 A | 8/2000 | Pfeifer | |
| 11,498,099 B2 * | 11/2022 | Kraus | ................... A61B 90/70 |
| 2007/0074742 A1 * | 4/2007 | Lin | ....................... A61B 90/70 |
| | | | 134/18 |
| 2013/0313154 A1 | 11/2013 | Hernandez et al. | |
| 2014/0099233 A1 * | 4/2014 | Bommarito | .............. C12Q 1/66 |
| | | | 435/31 |
| 2015/0257844 A1 | 9/2015 | Bommarito et al. | |
| 2016/0289732 A1 | 10/2016 | Bommarito et al. | |
| 2017/0121655 A1 | 5/2017 | Delplancke et al. | |
| 2020/0181679 A1 | 6/2020 | Bommarito et al. | |
| 2021/0068643 A1 * | 3/2021 | Spargo | ...................... A61L 2/18 |

FOREIGN PATENT DOCUMENTS

| | | | | |
|---|---|---|---|---|
| DE | 102009060836 A1 * | 6/2011 | .......... C12Q 1/6813 |
| JP | 2000-504416 A | 4/2000 | |
| JP | 2000-351682 A | 12/2000 | |
| JP | 2001-49716 A | 2/2001 | |
| JP | 2004-313552 A | 11/2004 | |
| JP | 2009-39192 A | 2/2009 | |
| JP | 2017-523276 A | 8/2017 | |
| JP | 2018-501814 A | 1/2018 | |
| WO | WO 00/09743 A1 | 2/2000 | |
| WO | WO 2007/122037 A1 | 11/2007 | |
| WO | WO 2016/159050 A1 | 10/2016 | |
| WO | WO-2017/006849 A1 | 1/2017 | |
| WO | WO 2017/134840 A1 | 8/2017 | |

OTHER PUBLICATIONS

DE-102009060836-A1, Machine Translation. (Year: 2025).*
Healthmark Industries, "Instructions for Use: Artificial Test Soil 2015 (ATS2015)". (Year: 2025).*
Lucas et al. ("Chemically defined, clinically relevant test soils for cleaning validation of reusable medical devices", Central Service Jun. 2015). (Year: 2015).*
CN-106370222-A, Machine Translation. (Year: 2025).*
International Search Report issued on Nov. 16, 2020 in PCT/EP2020/069257 filed on Jul. 8, 2020, 3 pages.
Blacky et al., "Leitlinie fuer die Pruefung von Reinigungs-Desinfektionsgeraeten mit thermischer Desinfektion fuer Steckbecken und Harnflaschen", Oesterreichische Gesellschaft fuer Sterilgutversorgung, 2017, Retrieved from the Internet: https://oegsv.com/wp/wp-content/uploads/10-OEGSV-LL-Pruefung-v.-RDG-S-2017.06-pdf [retrieved on Nov. 3, 2020], XP055746728, pp. 1-11.
Krueger et al., "Testanschmutzungen (TA) fuer die Kontrolle von Dekontaminatioinsgeraeten", EFHSS/SGSV Annual Conference 2003, Winterthur, Schweiz, 2003, Retrieved from the Internet: http://www.deconidi.ie/html/educ/lectures/efhss2003_0704_1205_Krueger_TesfanschmutzungenWDs_de.pdf [retrieved on Nov. 4, 2020], XP055747141, pp. 1-30.
DIN_ISO_TS_15883-5_Vornorm_Dokument_126881.pdf, Feb. 2006, 82 pages.
Norm_DIN EN ISO 15883.5_Entwurf, Jul. 2019, 102 pages.
Michelle J. Alfa et al., "Validation of ATS as an appropriate test soil to assess cleaning and sterilization efficacy in narrow lumened medical devices such as flexible endoscopes", Zentr Steril 2005; 13 (6), pp. 387-402.
English translation of the International Preliminary Report on Patentability and Written Opinion issued Jan. 20, 2022 in PCT/EP2020/069257, 9 pages.
Japanese Office Action issued Aug. 6, 2024 in Japanese Patent Application No. 2022-501220, 6 pages.

* cited by examiner (A)                                        (B)
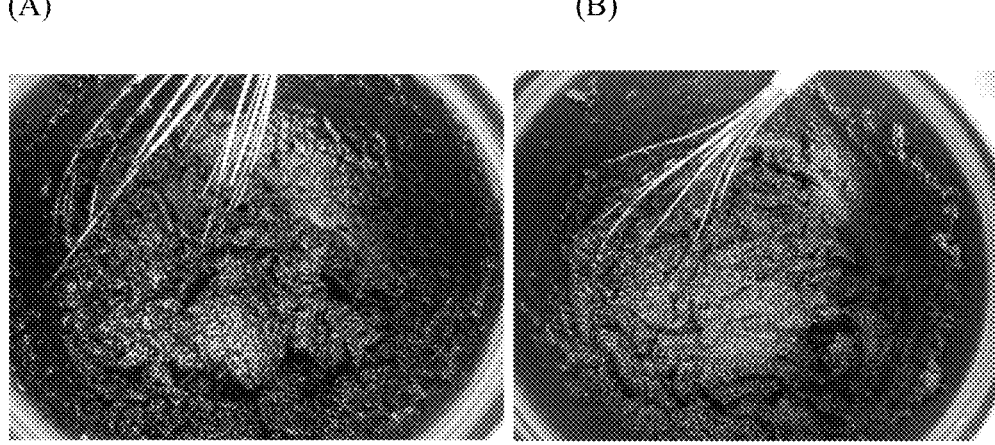

COMPOSITION FOR PRODUCTION OF A TEST SOIL FOR ASSESSMENT OF THE CLEANING ACTION OF CLEANING DEVICES AND USE THEREOF

CROSS-REFERENCE TO RELATED APPLICATIONS

The present application is the national stage of international application PCT/EP2020/069257, filed on Jul. 8, 2020, and claims the benefit of the filing date of German Appl. No. 10 2019 210 089.9, filed on Jul. 9, 2019.

TECHNICAL FIELD

The invention relates to a composition comprising the following constituents in dry form: (a) nigrosin, (b) wheat flour and (c) whole egg. The invention also relates to the use of the composition of the invention for production of test soil for assessment of the cleaning action of cleaning devices. Also provided is a method of producing a test soil for assessment of the cleaning action of cleaning devices for cleaning of vessels for human egesta, especially of washer-disinfectors, comprising the step of dissolving the composition as claimed of the invention in an aqueous medium. The invention relates to a test soil comprising the constituents of the composition of the invention in an aqueous medium, and to use thereof for assessment of the cleaning action of cleaning devices. Finally, the invention relates to a method of assessing the cleaning action of cleaning devices for cleaning of vessels for human egesta.

TECHNICAL BACKGROUND

The prior art includes a multitude of cleaning devices and cleaning methods for treatment of vessels for holding human egesta, for example bedpans or urine bottles. The vessels to be treated may contain relatively large amounts of liquid or amounts of solid wastes that typically have to be disposed of during cleaning. Moreover, such vessels may contain infectious wastes or be contaminated in some other way, such that, as well as emptying, disinfection is typically also required. Such cleaning devices for treatment of vessels for human egesta are accordingly frequently also referred to as cleaning and disinfection devices or else as washer-disinfectors (WDs). Since bedpans are among the items being cleaned in many cases, such devices are frequently also referred to as bedpan cleaners. Demands on such cleaning devices are fundamentally described in ISO standards series 15883.

For possible examples of cleaning and disinfection devices, reference may be made by way of example to DE 10 2004 056 052 A1, DE 103 48 344 A1, EP 1 824 373 B1, EP 2 755 695 B1, DE 10 2013 203 342 A1 or to DE 10 2013 208 060A1. The cleaning and disinfection devices described therein are also usable by way of example in the context of the present invention.

A significant challenge in respect of the construction and operation of cleaning and disinfection devices is that of the assurance of cleaning action and disinfecting action. In this regard, there exist numerous standards, specifications and recommendations. For example, DIN EN ISO 15883-6 generally describes the demands and test methods for WDs.

As well as the assurance of thermal disinfecting action, sufficient freedom from soiling should especially be assured. For example, the Deutsche Gesellschaft für Krankenhaushygiene [German Society for Hospital Hygiene] recommends the use of test soils in order to see visible residual staining.

Pre-standard CEN ISO/TS 15883-5 states that valid evidence for the cleaning efficacy of WDs according to ISO standards series 15883 is those test soils and methods that are currently being used in a number of countries, and national test soils are listed. For example, for bedpans and urine bottles in Germany, mixtures of bovine albumin, mucin, cornstarch and *E. faecium* are known. In Austria, test soils containing potato flakes, flour, nigrosin and egg are used for bedpans, called KMNE test soils, and mixtures of flour, nigrosin and egg for urine bottles, called MNE test soils. In addition, specifications with regard to the production of the test soils and the storage thereof are provided. This involves initial separate production and mixing of suspensions of nigrosin and wheat flour by boiling. Immediately prior to use, hens' eggs are added and the mixture is heated. In addition, the dry potato flakes are added if appropriate until the required consistency has been attained. Such test soils are then used to fill specimens in the form of bedpans or urine bottles with defined amounts, and the test soil is distributed in the test specimens. Subsequently, the WDs are fully loaded with the soiled test specimens, and an appropriate cleaning cycle is conducted. Subsequently, a sight test is undertaken, the criterion for acceptance being that there must no longer be any visible residues of the test soil on the test specimen.

A challenge in practice is that such test soils are complex to produce. The test soils may be stored in a refrigerator for not more than three days, and should in principle be used directly after production thereof. However, maintenance work and checks should generally be undertaken at the installation site of the cleaning devices. However, it is specifically there that requisite devices for production of the test soils are frequently unavailable. Furthermore, the production of such test soils is time-consuming and frequently constitutes a crucial step for the duration of the testing.

OBJECT OF THE INVENTION

It would therefore be desirable to provide test soils and methods of assessing the cleaning action of the cleaning devices for human egesta that largely avoid the disadvantages of known test soils and methods of the type specified. More particularly, the complexity involved in the provision of the test soils and the complexity involved in the performance of the entire method should be avoided.

DESCRIPTION OF THE INVENTION

This object is addressed by the embodiments according to the independent claims. Advantageous refinements, which are realizable individually or in any desired combination, are presented in the dependent claims.

In the following text, the terms "have", "comprise" or "include", or any grammatical variations thereof, are used in a non-exclusive manner. Accordingly, such expressions may refer both to situations in which no further features are provided in addition to the features introduced by such expressions, or to situations in which one or more further features are provided. For example, the expression "A has B", "A comprises B" or "A includes B" may relate both to the situation in which, apart from B, there is no further element in A (i.e. to a situation in which A consists exclusively of B) and to the situation in which, in addition to B, there are one or more further elements in A, for example element C, elements C and D or even further elements.

It is further pointed out that the expressions "at least one" and "one or more" and grammatical variants of such expressions, where used in connection with one or more elements or features or features and intended to express that the element or feature may be provided singly or multiply, are generally used only once, for example when the feature or element is introduced for the first time. When the feature or element is mentioned again later, the corresponding expression "at least one" or "one or more" will generally no longer be used, without restriction of the possibility that the feature or element may be provided singly or multiply.

Furthermore, the expressions "preferably", "in particular", "for example" or similar expressions hereinafter are used in connection with optional features, without alternative embodiments being restricted thereby. Accordingly, features introduced by such expressions are optional features, and it is not intended to restrict the scope of protection of the claims, and in particular of the independent claims, by way of such features. Accordingly, as a person skilled in the art will appreciate, the invention may also be implemented using other configurations. Similarly, features introduced by "in one embodiment of the invention" or by "in one working example of the invention" are to be understood as being optional features, without this being intended to restrict alternative configurations or the scope of protection of the independent claims. Furthermore, it is the intention that all possibilities of combining the features hereby introduced with other features, whether these be optional or non-optional features, remain unaffected by such introductory expressions.

The invention relates to a composition comprising the following constituents in dry form: (a) nigrosin, (b) wheat flour and (c) whole egg.

The expression "composition" describes a mixture of two or more constituents. The constituents may be present in different proportions. The constituents are preferably in dry form in the composition of the invention. The constituents may be in any dry form. Depending on the constituent, they may be in crystalline or amorphous form. The constituents may be in the form of crystalline or amorphous powder in the composition or in another suitable form, for example as fine powder, granular material or pellets. Typically, the composition according to the present invention is a free-flowing solid.

According to the invention, the term "dry form" is understood to mean that the constituents that are to be encompassed by the composition of the invention are to be essentially free of liquids, especially of aqueous solvents. "Essentially free of liquids" is understood here such that the residual liquid in the composition provided in accordance with the invention is insufficient to dissolve constituents, and so constituents in the composition may themselves also be in solid form.

The content of residual liquid may differ depending on the constituent. In the case of wheat flour, the residual liquid content is preferably not more than 20% by weight, not more than 15% by weight, not more than 10% by weight, not more than 5% by weight or more preferably not more than 2% by weight, based on the total weight of the constituent used in the composition. In the case of whole egg powder, the residual liquid content is preferably not more than 10% by weight, not more than 7% by weight, not more than 5% by weight or more preferably not more than 2% by weight, based on the total weight of the constituent used in the composition. Nigrosin powder is preferably free of detectable incorporated residual liquid. If water is incorporated, it is bound water of crystallization.

The term "nigrosin" as used herein refers to a blue-black anionic dye from the group of the diaminophenazine compounds that is water-soluble. As well as water-soluble nigrosin, there are also nigrosins that are alcohol- or oil-soluble. In the context of the invention, preference is given to a water-soluble nigrosin with CAS number 8005-03-6. Nigrosins are commercially available. Nigrosins can be obtained by heating nitrobenzene, aniline and aniline hydrochloride with metallic iron and iron(III) chloride. Particularly preferred nigrosins are described in detail in the working examples.

The term "wheat flour" is a powder formed in the grinding of wheat grains. The term as used here encompasses flours of all types of wheat, including the subspecies of spelt, emmer or einkorn. Wheat flours are typified depending on their caking properties, their fineness, i.e. the particle size, their ash content and their protein content. The wheat flour may preferably be fine, semi-coarse or coarse wheat flour. The flour used in accordance with the invention is preferably a type 405 wheat flour. Other types that may likewise be used are types 550, 812, 1050 or 1600. Particularly preferred wheat flour is described in detail in the working examples.

The term "whole egg" as used here refers to a preparation including essentially the constituents of eggs (yolk and white). More particularly, the preparation should encompass the proteins, lipids and carbohydrates from eggs. Preferably in accordance with the invention, the eggs are hens' eggs, although it is also possible to use other eggs, especially poultry eggs, e.g. quail eggs or ostrich eggs. According to the invention, the constituents of the whole egg are likewise in essentially dry form. For this purpose, whole egg can be dried by suitable methods. These include, for example, lyophilization methods. According to the invention, the term also encompasses whole egg substitutes, e.g. vegetarian or vegan whole egg, or artificial compositions comprising the constituents of whole egg. More preferably, the whole egg in the context of the invention is hens' egg powder. Particularly preferred whole egg is described in detail in the working examples.

The composition of the invention may be dissolved in aqueous solvents such as water or aqueous buffer solutions. For this purpose, the composition is dissolved in a suitable amount of the aqueous solvent. The dissolving operation may be assisted here by suitable measures, for example automatic or manual stirring. The dissolved composition may then be used as test soil in order to assess the cleaning performance of cleaning devices for cleaning of vessels for human egesta. Depending on the composition, it is possible to assess cleaning performance for bedpans or urine bottles. Suitable methods are likewise described elsewhere herein.

The composition of the invention may be provided as a ready-made mixture of constituents. For this purpose, the constituents of the composition can be mixed with one another in suitable, essentially dry form, for example as a powder, preferably so as to give rise to a homogeneous mixture of the constituents. This can then be provided in suitable packaging. The packaging here should prevent the composition from becoming moist and hence prevent occurrence of unwanted dissolution of constituents. Alternatively, the constituents of the composition of the invention may also be provided individually in suitable packaging, for example as what is called a kit. In this case, the composition is provided from the individual constituents before or on production of the test soil. Typically, the constituents are provided here in predefined amounts, such that the provision of the composition from the constituents does not require measurement of the constituents, but can be accomplished by simple mixing of the packaged individual constituents in the dry state or by direct dissolution in an aqueous solvent.

Advantageously, the composition of the invention, which does of course consist of essentially dry constituents, can be stored over a long period. Test stains in current use comprise liquid whole egg and accordingly have only limited shelf life as aqueous compositions. The composition of the invention additionally permits the provision of a standardized test soil since the constituents of the composition have good dissolvability in a defined amount of an aqueous solvent. It is thus possible to very substantially avoid variations or problems in the dissolving operation, as can occur when liquid whole egg is used.

The composition of the invention may preferably be provided in the form of portioned units. A "portioned unit" in the context of the present invention may preferably be understood to mean a particular amount of the composition. More preferably, a "portioned unit" includes the amount of the composition required, based on a volume of 250 ml of aqueous solvent to be added. Most preferably, a portioned unit contains an amount of the composition of 47.8 g to 62.2 g and most preferably 55 g.

Portioned units may be advantageous since the user does not have to weigh out the amount of the test soil needed. It is thus possible to additionally simplify the handling and use of the test soil.

The portioned units may be packaged in a suitable manner. Particularly suitable forms of packaging are portion packs, or units portioned in another form of packaging, such as bags, sachets, tubes, cups, cartons. Accordingly, the composition of the invention may especially take the form of a portioned unit, preferably a portion pack.

The abovementioned suitable forms of packaging may be provided with an identifier, for example an overprint, tag, sticker or label, comprising a graphic code and/or an RFID tag. The graphic code may, for example, be a one-dimensional barcode or a two-dimensional QR code. This code, when read with a smartphone or another mobile terminal for example, may lead to an Internet site, such as a web site, where instructions for use of the test soil and performance of the test can be displayed to the user. The RFID tag, when read with a smartphone or another mobile terminal for example, may also give the user instructions as to how the test soil should be applied and/or how the test is to be conducted. This can additionally simplify the handling and use of the test soil.

Preferred embodiments of the composition of the invention are described hereinafter.

Nigrosin and whole egg are preferably in powder form. More preferably, the constituents are present in the composition in the following amounts, based in each case on a volume of 250 ml of aqueous solvent to be added: (a) nigrosin 0.8 g to 1.2 g, preferably 1.0 g, (b) wheat flour 30 g to 40 g, preferably 35 g, and (c) whole egg 17 g to 21 g, preferably 19 g. The composition thus has a total weight of 47.8 g to 62.2 g and preferably 55 g. In a preferred embodiment, the proportion of nigrosin is thus about 1.8% by weight, the proportion of wheat flour about 63.6% by weight, and the proportion of whole egg about 34.6% by weight. The composition according to the present invention may be processed correspondingly for any volumes of aqueous solvent; see above, now in the definition of wheat flour.

The composition preferably comprises dried potato flakes as an additional constituent. Typically, the dried potato flakes are present in an amount of 35 g to 45 g, preferably 40 g, based on a volume of 250 ml of aqueous solvent to be added. In that case, this composition of the invention has a total weight of 82.8 g to 107.2 g and preferably 95 g. In a preferred embodiment, the proportion of nigrosin is thus about 1.0% by weight, the proportion of wheat flour about 36.9% by weight, the proportion of whole egg 20% by weight, and the proportion of dried potato flakes 42.1% by weight.

The term "dried potato flakes" as used here refers to aggregates composed of essentially dry potato cells. Dried potato flakes are commercially available and are produced by processes known in the art. Typically, for this purpose, potatoes are boiled and processed to slurry. This slurry is dried to a thin layer on roll dryers and comminuted to flakes of the desired size. By means of process technology, it is possible to destroy a different proportion of the potato cells. In this way, it is also possible to adjust the starch content differently. Particularly preferred dried potato flakes are described in detail in the working examples. But the term also includes potato powders.

The invention also relates to the use of a composition as described above, comprising the following constituents in dry form: (a) nigrosin, (b) wheat flour and (c) whole egg, for production of test soil for assessment of the cleaning action of cleaning devices for cleaning of urine bottles for human egesta.

It will be apparent here that the test soil must first be provided by dissolving the composition of the invention in an aqueous solvent. This can be accomplished by the methods described herein. The test soil is preferably produced by dissolving the composition in an aqueous medium; more preferably, the aqueous solvent here is water or an aqueous buffer solution. The test soil is then used to assess the cleaning action of cleaning devices. For this purpose, the test soil is applied to the urine bottle. This can be effected homogeneously or at points on an inner and/or outer surface of the urine bottle. Methods of applying the test soil are known to those skilled in the art.

The expression "cleaning device" as used here is a broad expression to which should be ascribed its usual and standard meaning as understood by a person skilled in the art. The expression is not restricted to a specific or adapted meaning. The expression may, without limitation, refer in particular to a device set up to free material to be cleaned from contaminants. The cleaning device may especially comprise at least one cleaning chamber for accommodating the material to be cleaned, and a contacting device with which the material to be cleaned is contacted with at least one cleaning fluid, for example at least one cleaning liquid and/or steam. For examples of possible cleaning devices, reference may be made to the above-cited prior art.

Possible material to be cleaned in the context of the invention includes all articles as customarily understood by the person skilled in the art. The expression is not restricted to a specific or adapted meaning. The expression may, without restriction, relate in particular to vessels which may be used, for example, in the hospital or care sector and which can hold, for example, solid or liquid egesta in an amount of at least 100 ml, especially in an amount of 200 ml or even 500 ml. More particularly, these vessels may be bedpans and/or urine bottles.

Accordingly, the cleaning device may especially be configured as a washer-disinfector within the scope, for example, of ISO standards series 15883 Washer-disinfectors—Part 1: General requirements, terms and definitions and tests.

The expression "test soil" as used here is a broad expression to which should be ascribed its usual and standard meaning as understood by a person skilled in the art. The test soil in the context of the invention comprises the composition of the invention in dissolved form as described herein. The test soil is suitable for wetting of a test specimen. In addition, the removal of the test soil from the test specimen by a cleaning method to be assessed or by a cleaning device to be assessed is detectable. The test soil may especially be configured as a pasty mass visible to the human eye.

The expression "test specimen" as used here is a broad expression to which should be ascribed its usual and standard meaning as understood by a person skilled in the art. The expression is not restricted to a specific or adapted meaning. The term may, without restriction, relate in particular to a device or an element which can be subjected to a cleaning method and which has at least one surface cleaned during the cleaning method to which a test soil may be applied prior to the cleaning. In particular, the test specimen may be a vessel for holding human egesta, especially a bedpan and/or a urine bottle. Accordingly, the test specimen may especially be a test specimen within the scope of pre-standard DIN ISO/TS 15883-5, Washer-disinfectors—Part 5: Test soils and methods for demonstrating cleaning efficacy.

The invention further relates to the use of a composition as described above, comprising the following constituents in dry form: (a) nigrosin, (b) wheat flour and (c) whole egg, and dried potato flakes as an additional constituent, for production of test soil for assessment of the cleaning action of cleaning devices for cleaning of vessels for human egesta.

The invention also relates to a method of producing a test soil for assessment of the cleaning action of cleaning devices for cleaning of vessels for human egesta, especially of washer-disinfectors, comprising the step of dissolving the composition of the invention in an aqueous medium.

The aqueous medium is preferably water or an aqueous buffer solution. The composition of the invention is introduced into and dissolved in the aqueous medium. The dissolving operation may be assisted here by physical methods. For this purpose, the dissolving of the constituents of the composition of the invention can be conducted by manual or automatic stirring. Both manual stirrers and automatic stirrer devices suitable for the dissolving operation in the context of the invention are known to the person skilled in the art. The dissolving can additionally be promoted by heating the solution during the dissolving or by the use of heated aqueous medium as solvent. Typically, the solution or solvent here is heated to a temperature in the range from 20° C. to 40° C., preferably below 35° C., more preferably 25° C., 28° C., 30° C. or 35° C.

The invention further relates to a test soil for assessing the cleaning action of cleaning devices for cleaning of vessels for human egesta, especially of washer-disinfectors, comprising the constituents of the composition of the invention in an aqueous medium, preferably water, or obtainable by the method of the invention.

The invention relates to the use of the test soil of the invention for assessing the cleaning action of cleaning devices for cleaning of vessels for human egesta.

The test soil may comprise the constituents (a) nigrosin, (b) wheat flour and (c) whole egg of the composition of the invention in an aqueous medium, preferably water. By means of this test soil, the cleaning action of cleaning devices for cleaning of urine bottles is preferably assessed.

The test soil may comprise the constituents (a) nigrosin, (b) wheat flour and (c) whole egg of the composition of the invention and additionally dried potato flakes in an aqueous medium, preferably water. By means of this test soil, the cleaning action of cleaning devices for cleaning of bedpans is preferably assessed.

The invention finally also relates to a method of assessing the cleaning action of cleaning devices for cleaning of vessels for human egesta, especially of washer-disinfectors, comprising:

(a) producing test soil by a method of the invention as described above;

(b) applying the test soil produced in step (a) to vessels for human egesta, especially bedpans or urine bottles;

(c) cleaning the vessels from step (c) by means of a cleaning device to be assessed; and (d) assessing the cleaning action of the cleaning device for cleaning vessels for human egesta by the amount of test soil present or removed.

The method of the invention for assessing the cleaning action of cleaning devices may preferably be used here in order to assess the cleaning action for bedpans and/or urine bottles based on human egesta. Depending on the type of egesta or the type of item to be cleaned (bedpan or urine bottle), it is possible to select a correspondingly suitable composition of the invention. For urine bottles preference is given to using a composition without dried potato flakes, and for bedpans one comprising dried potato flakes.

The correspondingly chosen composition of the invention is first used to produce a test soil by dissolving the composition in an aqueous medium as described herein.

This test soil is applied to the respective test specimens and dried on. The application can be effected here homogeneously or at points on one or more inner and/or outer surfaces. The test soil is preferably dried on for about 5 to 10 min, more preferably 5 to 7 min. In this state, the test soil preferably enters into a firm bond, but one which is reversible by the cleaning operation, with the surface of the test specimen.

The test specimens thus produced are cleaned in the cleaning device to be assessed with a suitable cleaning program.

The cleaned test specimens are then assessed with regard to the cleaning performance of the cleaning device or the cleaning program used. For this purpose, preferably, the amount of the test soil present or removed on the test specimens is determined and compared with a reference. A reference used may be a test specimen without test soil or an uncleaned test specimen with test soil. Alternatively, the reference may also be a state defined for the test specimen. The comparison here may be made by inspection or by comparison, preferably automated comparison, of measured parameters that are indicators of the presence or absence of the test soil. Suitable parameters here may be parameters from the evaluation of image data or optical measurements. Appropriate methods are well known to those skilled in the art.

The amount of test soil removed can be used to assess the cleaning performance. The amount removed can serve here as an assessment indicator for cleaning performance, with a large amount of test soil removed being an indicator of good cleaning performance, and a small amount of test soil removed an indicator of poor cleaning performance. For this purpose, it is possible to use a scoring system wherein the cleaning performance is classified in various categories depending on the amount of test soil removed.

In summary, and without limitation of further possible configurations, the following embodiments in particular are described:

Embodiment 1: A composition comprising the following constituents in dry form: (a) nigrosin, (b) wheat flour and (c) whole egg.

Embodiment 2: The composition according to embodiment 1, wherein nigrosin and whole egg are in powder form.

Embodiment 3: The composition according to embodiment 1 or 2, wherein the constituents are present in the composition in the following amounts, based in each case on a volume of 250 ml of aqueous solvent to be added: (a) nigrosin 0.8 g to 1.2 g, preferably 1.0 g, (b) wheat flour 30 g to 40 g, preferably 35 g, and (c) whole egg 17 g to 21 g, preferably 19 g.

Embodiment 4: The composition according to any of embodiments 1 to 3, wherein the composition comprises dried potato flakes as an additional constituent.

Embodiment 5: The composition according to embodiment 4, wherein the dried potato flakes are present in an amount of 35 g to 45 g, preferably 40 g, based on a volume of 250 ml of aqueous solvent to be added.

Embodiment 6: The composition according to any of embodiments 1 to 5, wherein the composition takes the form of a portioned unit, preferably a portion pack, or of units portioned in another form of packaging, such as bags, sachets, tubes, cups, cartons.

Embodiment 7: The composition according to embodiment 6, wherein the package is provided with a label comprising a graphic code and/or an RFID tag.

Embodiment 8: The use of the composition according to any of embodiments 1 to 3 for production of test soil for assessment of the cleaning action of cleaning devices for cleaning of urine bottles for human egesta.

Embodiment 9: The use of the composition according to embodiment 4 or 5 for production of test soil for assessment of the cleaning action of cleaning devices for cleaning of bedpans for human egesta.

Embodiment 10: The use according to embodiment 8 or 9, wherein the test soil is produced by dissolving the composition in an aqueous medium.

Embodiment 11: A method of producing a test soil for assessment of the cleaning action of cleaning devices for cleaning of vessels for human egesta, especially of washer disinfectors, comprising the step of dissolving the composition according to any of embodiments 1 to 5 in an aqueous medium.

Embodiment 12: The method according to embodiment 11, wherein the aqueous medium includes water or an aqueous buffer solution.

Embodiment 13: A test soil for assessing the cleaning action of cleaning devices for cleaning of vessels for human egesta, especially of washer-disinfectors, comprising the constituents of the composition according to any of embodiments 1 to 5 in an aqueous medium, preferably water, or obtainable by the method according to embodiment 11 or 12.

Embodiment 14: The use of the test soil according to embodiment 13 for assessment of the cleaning action of cleaning devices for cleaning of urine bottles or bedpans for human egesta.

Embodiment 15: The use according to embodiment 14, wherein the test soil comprises the constituents of the composition according to any of embodiments 1 to 3 in an aqueous medium, preferably water, and the cleaning action of cleaning devices for cleaning of urine bottles for human egesta is assessed.

Embodiment 16: The use according to embodiment 14, wherein the test soil comprises the constituents of the composition according to embodiment 4 or 5 in an aqueous medium, preferably water, and the cleaning action of cleaning devices for cleaning of bedpans for human egesta is assessed.

Embodiment 17: A method of assessing the cleaning action of cleaning devices for cleaning of vessels for human egesta, especially of washer-disinfectors, comprising:

(a) producing test soil by a method according to embodiment 11 or 12;

(b) applying the test soil produced in step (a) to vessels for human egesta, especially bedpans or urine bottles;

(c) cleaning the vessels from step (c) by means of a cleaning device to be assessed; and (d) assessing the cleaning action of the cleaning device for cleaning vessels for human egesta by the amount of test soil present or removed.

FIG. 1 shows a visual comparison of the test soils according to KMNE (Koller) (A) and according to the present invention (B).

DESCRIPTION OF THE WORKING EXAMPLES

The examples that follow are intended to illustrate the invention. They do not serve in any way to restrict the scope of protection.

Example 1: Test Soil for Bedpans

Test soil for the bedpan: 1.0 g of nigrosin powder (C.I.50420, water-soluble for microscopy), 35 g of type 405 wheat flour, 40 g of dried potato flakes (potato purée), 19 g of dried whole egg powder (spray-dried): Mix well, can be stored in airtight packaging for about 12 months and used. Before use, add the mixture to a pot and stir up with 250 ml of lukewarm water with an egg whisk for 2-3 min. In order to test the consistency of the mass, the loops of the egg whisk are first immersed fully into the mass and then pulled back out of the mass. If the mixture has the right consistency, it flows gradually down the loops of the egg whisk, and after 5-10 seconds the lump of mixture remaining in the egg whisk has a diameter of 40-50 mm. Sufficient as soil for 1-2 bedpans or commode pans. Apply mass to the bedpans or commode pans as instructed. After application, allow the mass to dry on for 5-7 min. This prepared mass should be used within 3-4 hours.

Example 2: Test Soil for Urine Bottles

Test soil for the urine bottle: 1.0 g of nigrosin powder (C.I.50420, water-soluble for microscopy), 35 g of type 405 wheat flour, 19 g of dried whole egg powder (spray-dried): Mix well, can be stored in airtight packaging for about 12 months and used. Before use, add the mixture to a pot and stir up with 250 ml of lukewarm water with an egg whisk for 2-3 min. Apply mass into/onto the urine bottle as instructed. After application, allow the mass to dry on for 5-7 min. This prepared mass should be used within 3-4 hours.

Example 3: Test of Cleaning Action

Test soils are produced as described in examples 1 and 2 and applied to and dried onto bedpans or urine bottles. The test specimen is thus prepared are subjected to a cleaning and disinfection method in a cleaning device in a suitable manner. Using the test soil remaining on the test specimens (before-after comparison), it is possible to assess the cleaning performance.

Example 4: Comparison of the Test Soil for
Bedpans According to Koller with

Formulation for KMNE protection for testing of cleaning
and disinfection (Koller):

1. Nigrosin solution Stir 6 g of nigrosin powder into 276
   ml of hand-hot water.
2. Flour paste: Stir 53 g of coarse wheat flour into 369 ml
   of cold water and boil for about three minutes.
3. Mix the solution and the paste well and allow to cool
   down to room temperature (about 35°).
4. Mix three whisked fresh eggs into the mass and then stir
   in 100 g of potato dough flakes in small portions. 35°).

Final consistency as stool substitute: When an egg whisk
is immersed—from a depth of 7 cm—a lump of diameter 4
to 5 cm should remain suspended for 5 to 10 seconds.

This mass was compared to a mass produced as described
in example 1. The results are shown in FIG. 1. There is no
significant difference with regard to the properties of rel-
evance for testing.

The invention claimed is:

1. A composition, comprising, as constituents in dry form:
   (a) 1.8 wt % nigrosin;
   (b) 63.6 wt % wheat flour; and
   (c) 34.6 wt % whole egg, each weight percentage relative
   to a total weight of the composition,
   wherein the composition is suitable as a test soil for
   assessment of a cleaning action of cleaning devices for
   cleaning of vessels for human egesta.

2. The composition of claim 1, wherein nigrosin and
whole egg are in powder form.

3. The composition of claim 1, in form of a portioned unit
in a package.

4. The composition of claim 3, wherein the package
comprises a label comprising a graphic code and/or an RFID
tag.

5. A method of assessing cleaning action in a cleaning
device, the method comprising:
   producing test soil with the composition of claim 1, the
   test soil being used for assessment of the cleaning
   action of cleaning devices for cleaning urine bottles for
   human egesta.

6. The method of claim 5, wherein the test soil is produced
by dissolving the composition in an aqueous medium.

7. A method of producing a test soil for assessment of a
cleaning action of cleaning devices for cleaning of vessels
for human egesta, the method comprising:
   dissolving the composition of claim 1 in an aqueous
   medium.

8. The method of claim 7, wherein the aqueous medium
comprises water or an aqueous buffer solution.

9. A method of assessing a cleaning action of a cleaning
device configured for cleaning of a vessel suitable for human
egesta, the method comprising:
   (a) producing test soil by the method of claim 7;
   (b) applying the test soil from the producing (a) to one or
   more vessels suitable for human egesta;
   (c) cleaning the one or more vessels from the applying (c)
   with a cleaning device to be assessed; and (d) assessing the cleaning action of the cleaning device
   from the cleaning (c) based on an amount of test soil
   present or removed.

10. A test soil suitable for assessing cleaning action of a
cleaning device configured for cleaning one or more vessels
for human egesta, the soil comprising:
   the constituents of the composition of claim 1 in an
   aqueous medium.

11. A method of assessing cleaning action in a cleaning
device, the method comprising:
   contacting the test soil of claim 10 with a urine bottle or
   bedpan to thereby assess cleaning action of a cleaning
   device configured for cleaning urine bottles or bedpans
   for human egesta.

12. The method of claim 11, wherein the cleaning action
on the urine bottles is assessed.

13. The method of claim 11, wherein the cleaning action
on the bedpans is assessed.

14. A composition, comprising, as constituents in dry
form:
   (a) 1.0 wt % nigrosin;
   (b) 36.9 wt % wheat flour;
   (c) 20 wt % whole egg; and
   (d) 42.1 wt % potato flakes, each weight percentage
   relative to a total weight of the composition,
   wherein the composition is suitable as a test soil for
   assessment of a cleaning action of cleaning devices for
   cleaning a bedpan for human egesta.

15. The composition of claim 14, wherein nigrosin and
whole egg are in powder form.

16. The composition of claim 14, in form of a portioned
unit.

17. A method of assessing cleaning action in a cleaning
device, the method comprising:
   producing test soil with the composition of claim 14, the
   test soil being used for assessment of the cleaning
   action of cleaning devices for cleaning urine bottles for
   human egesta.

18. The method of claim 17, wherein the test soil is
produced by dissolving the composition in an aqueous
medium.

19. A method of producing a test soil for assessment of a
cleaning action of cleaning devices for cleaning of vessels
for human egesta, the method comprising:
   dissolving the composition of claim 14 in an aqueous
   medium.

20. A method of assessing a cleaning action of a cleaning
device configured for cleaning of a vessel suitable for human
egesta, the method comprising:
   (a) producing test soil by the method of claim 19;
   (b) applying the test soil from the producing (a) to one or
   more vessels suitable for human egesta;
   (c) cleaning the one or more vessels from the applying (c)
   with a cleaning device to be assessed; and
   (d) assessing the cleaning action of the cleaning device
   from the cleaning (c) based on an amount of test soil
   present or removed.

* * * * *